United States Patent [19]
Grollier et al.

[11] Patent Number: 5,139,037
[45] Date of Patent: Aug. 18, 1992

[54] COSMETIC COMPOSITION FOR TREATING KERATIN FIBRES, AND PROCESS FOR TREATING THE LATTER

[75] Inventors: Jean F. Grollier, Paris; Claude Dubief, Versailles, both of France

[73] Assignee: L'Oreal, Paris, France

[21] Appl. No.: 902,670

[22] Filed: Sep. 2, 1986

Related U.S. Application Data

[63] Continuation of Ser. No. 457,267, Jan. 11, 1983, abandoned.

[30] Foreign Application Priority Data

Jan. 15, 1982 [LU] Luxembourg .......................... 83876

[51] Int. Cl.$^5$ ............................................... A45D 7/04
[52] U.S. Cl. ................................... 132/203; 132/204; 132/205; 132/206
[58] Field of Search ................ 132/203, 204, 205, 206

[56] References Cited

FOREIGN PATENT DOCUMENTS

| | | |
|---|---|---|
| 0047714 | 3/1982 | European Pat. Off. . |
| 0080976 | 6/1983 | European Pat. Off. . |
| 0080977 | 6/1983 | European Pat. Off. . |
| 2470596 | 6/1981 | France . |
| 54-41909 | 11/1979 | Japan . |
| 56-92811 | 7/1981 | Japan . |
| 57-48335 | 3/1982 | Japan . |
| 2043077 | 10/1980 | United Kingdom . |
| 2063671 | 6/1981 | United Kingdom . |
| 3217059 | 11/1982 | United Kingdom . |

*Primary Examiner*—V. Millin
*Attorney, Agent, or Firm*—Fleit, Jacobson, Cohn, Price, Holman & Stern

[57] ABSTRACT

Cosmetic compositions for treating the hair, nails and skin are described which contain, in a solvent medium, at least one amphoteric polymer of betainised dialkylaminoalkyl (meth)acrylate or dialkylaminoalkyl(meth)acrylamide, containing at least units of the formula:

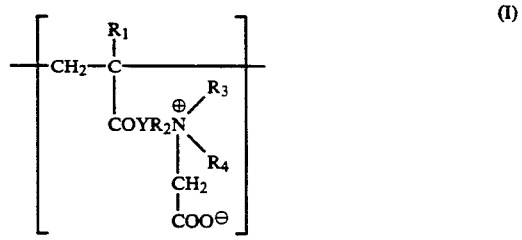

in which $R_1$ denotes a hydrogen atom or a methyl group, $R_2$ denotes an alkylene group having 1 to 4 carbon atoms, Y denotes O or NH and $R_3$ and $R_4$ independently of one another denote hydrogen or alkyl having 1 to 4 carbon atoms, and at least one cationic derivative.

23 Claims, No Drawings

COSMETIC COMPOSITION FOR TREATING KERATIN FIBRES, AND PROCESS FOR TREATING THE LATTER

This is a continuation of application Ser. No. 457,267 filed Jan. 11, 1983, now abandoned.

The present invention relates to cosmetic compositions which can be used for treating keratin substances and which are more particularly intended for treating the hair, skin and nails.

It is well known that keratin fibres, and in particular, hair, are usually sensitised to various degrees by the action of atmospheric agents and also by treatments such as bleaching, perming and/or dyeing, so that the hair is frequently difficult to comb out and style.

One of the means commonly used for improving the comb-out and softness of sensitised hair consists in using cationic surface-active agents.

However, it is known that the use of such compounds has the disadvantage of weighing the hair down considerably and of having an adverse effect on the hold, the body and the liveliness of the hair. As a result, the hair does not easily retain the style or shape which it has been given.

These same disadvantages are particularly visible in the case of fine hair, which lacks bulk, body and hold.

Furthermore, it has already been proposed to improve the comb-out and softness of the hair by using cationic polymers. However, these polymers have the disadvantage of not giving the hair sufficient hold.

To make the style hold, it has also already been recommended to use amphoteric polymers such as those mentioned in U.S. Pat. No. 4,075,131 or French Certificate of Addition No. 2 280 361.

Compositions containing only these polymers do not, however, make it possible to obtain sufficient softness and adequate comb-out.

Furthermore, French Specification No. 2 470 596, describes with use of amphoteric polymers with cationic polymers. Although the polymers disclosed make it possible to obtain good results as regards the comb-out and hold, the treated hair nevertheless has insufficient liveliness and insufficient stiffness.

We have not just discovered, surprisingly, that the use of amphoteric polymers of betainised dialkylaminoalkyl (meth)acrylate or dialkylaminoalkyl (meth)acrylamide in combination with a cationic derivative makes it possible to improve the liveliness, the shine, the body and the stiffness of the hair treated with this combination. Furthermore, the hair treated in this way possesses noteworthy comb-out properties in addition to the properties mentioned above. The hair is moreover soft to the touch and retains these properties with time.

The compositions for treating keratin substances, and in particular the hair, nails or skin, according to the present invention, are essentially characterised in that they contain, in a solvent medium, generally an aqueous, alcoholic or aqueous-alcoholic solution, which may or may not be thickened to give a cream, a gel, an emulsion or a foam, for instance, at least one amphoteric polymer of betainised dialkylaminoalkyl (meth)acrylate or dialkylaminoalkyl(meth)acrylamide containing at least units of the formula:

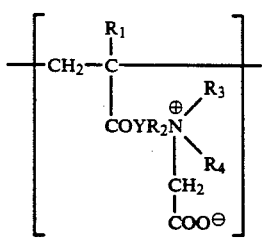

in which $R_1$ denotes a hydrogen atom or a methyl group, $R_2$ denotes an alkylene group having 1 to 4 carbon atoms, Y denotes O or —NH— and $R_3$ and $R_4$ independently of one another denote hydrogen or alkyl having 1 to 4 carbon atoms, and at least one cationic derivative consisting of a cationic surface-active agent containing at least one nitrogen atom joined to one or more fatty chains and optionally quaternised, or consisting of a cationic polymer of the polyamine, polyaminopolyamide or poly-(quaternary ammonium) type, the amine or ammonium groups forming part of the polymer chain or being joined thereto.

The abovementioned amphoteric polymers are typically used in an amount from 0.01 to 10% by weight, relative to the total weight of the composition. The cationic derivatives are typically used in an amount from 0.01 to 10%, and preferably 0.05 to 5%, by weight.

The amphoteric polymers usually have a molecular weight of 500 to 2,000,000 while the cationic polymers usually have a molecular weight of 500 to 2,000,000.

The amphoteric polymers containing units corresponding to the above formula (I) are generally in the form of copolymers which contain, in addition to the units of the abovementioned formula (I), at least units of the formula:

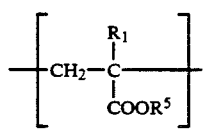

in which $R_1$ is as defined above and $R_5$ represents an alkyl or alkenyl radial having from 4 to 24 carbon atoms or a cycloalkyl radical having from 4 to 24 carbon atoms.

It is also possible to use terpolymers tetrapolymers or pentapolymers which contain, in addition to the units (I) and (II) defined above, units of the formula:

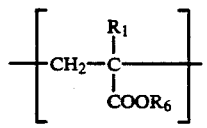

in which $R_6$ preferably denotes an alkyl or alkenyl group having 1 to 3 carbon atoms and $R_1$ is as defined above, and/or units derived from a hydrophilic ethylenic monomer (IV), and/or units of a second ethylenic monomer (V) which is different from the abovementioned units.

The units of the formula I are preferably present in an amount of 25 to 45% by weight and the units of the formula (II) are preferably present in an amount of 5 to 65% by weight.

The units of the formula (III) are preferably present in an amount up to 50% by weight, while the units (IV) and (V) are generally present in an amount up to 20% by weight, relative to the total weight of the polymer.

These polymers can be prepared in known manner by copolymerising the various monomers in a hydrophilic solvent in a first step. In a second step, the polymer thus formed in reacted, as a solution in a hydrophilic solvent, with a halogenoacetate of the formula:

$$XCH_2COOM \qquad (IV)$$

in which X denotes a halogen atom such as chlorine, bromine or iodine and M denotes an alkali metal, in particular sodium or potassium.

A particularly preferred polymer is the copolymer containing units of the formulae (I), (II) and (III) in which Y denotes an oxygen atom, $R_2$ denotes the group $-C_2H_4-$, $R_1$, $R_3$ and $R_4$ denote methyl, $R_5$ denotes an alkyl group having 4 to 18 carbon atoms and $R_6$ denotes an alkyl group having 1 to 3 carbon atoms. The average molecular weight of this polymer is preferably from 70,000 to 90,000.

This polymer is sold under the trademark "AMPHO-SET" by the firm Mitsubishi Petrochemical Co Ltd or under the Trademark "AMERSETTE" by the firm Amerchol.

Monomers from which the units of the formula (I) may be derived include, in particular, dimethylaminomethyl acrylate or methacrylate, diethylaminoethyl acrylate or methacrylate, dimethylaminopropyl acrylate or methacrylate, dimethylaminoethylacrylamide or dimethylaminomethylmethacrylamide and diethylaminopropylacrylamide or diethylaminopropylmethacrylamide. The proportion is preferably from 30 to 40% by weight, relative to the total weight of the monomers used.

The monomer of the formula (II) is an acrylic or methacrylic acid ester, in particular 2- ethylhexyl acrylate or methacrylate, stearyl acrylate or methacrylate, lauryl acrylate or methacrylate, isobutyl acrylate or methacrylate, cyclohexyl acrylate or methacrylate and oleyl arcylate or methacrylate. This monomer is preferably present in proportions of 10 to 50% by weight, relative to the total weight of the monomers used.

The monomers of the formula (III) are methacrylic or acrylic acid esters, preferably methyl acrylate or methacrylate, ethyl acrylate or methacrylate, propyl acrylate or methacrylate, butyl acrylate or methacrylate and allyl acrylate or methacrylate. These monomers are preferably used in proportions of 5 to 40% by weight, relative to the total weight of the monomers used.

The monomers of the formula (IV) are preferably chosen from N-vinylpyrrolidone, acrylamide, hydroxyethyl or hydroxypropyl acrylate or methacrylate and polyethylene glycol or polypropylene glycol monoacrylate or monomethacrylate. The monomers of formula (V) used are preferably chosen from acrylonitrile, styrene chlorostyrene, vinyltoluene, vinyl acetate, polypropylene glycol monoacrylate or monomethacrylate, vinyltrichlorosilane and methacryloxypropyltrimethoxysilane.

These polymers can be prepared by polymerisation in a hydrophilic solvent, in particular an aliphatic alcohol, preferably having from 1 to 4 carbon atoms, such as monoalcohols such as ethanol, isopropanol and methanol, polyalcohols such as ethylene glycol and ethylene glycol ethyl ether or butyl ether, esters such as methyl acetate, dioxane and dimethylformamide. These solvents can also be used in mixtures with water.

The cationic polymers used in combination with the abovementioned amphoteric polymers are generally the polymers having a molecular weight of 500 to 2,000,000 which are described in French Specifications Nos. 2,,007,143, 1,492,597, 2,162,025, 2,280,361, 2,252,840, 2,368,4508, 1,583,363, 2,080,759, 2,190,406, 2,320,330, 2,270,846, 2,316,271, 2,336,434, 2,189,434 and 2,413,907 and U.S. Pat. Nos. 3,589,978, 4,031,307, 3,227,615, 2,961,347, 2,273,780, 2,375,853, 2,388,614, 2,454,547, 3,206,462, 2,261,002, 2,271,378, 3,874,870, 4,001,432, 3,929,990, 3,996,904, 4,005,193, 4,025,617, 4,026,627, 4,025,653, 4,026,945 and 4,072,020, the disclosure of which is hereby incorporated by reference.

The cationic polymers use in the composition of the invention are polymers of the polyamine, polyaminoamide or poly-(quaternary ammonium) type, the amine or ammonium group forming part of the polymer chain or being joined thereto, but are not quaternary cellulose ethers.

Polymers of this type which can be used according to the invention include:

1.) Vinylpyrrolidone/dialkylaminoalkyl acrylate or methacrylate copolymers (quaternised or unquaternised), such as those sold under the name Gafquat by the Gaf Corp, such as "copolymer 845" and "Gafquat 734 or 755" described in greater detail in particular in French Patent 2,077,143 and French Patent Application 2,393,573.

2.) Cationic cellulose derivatives, such as CELQUAT L 200 and CELQUAT H 100 sold by National Starch.

3.) Cationic polysaccharides, such as those described in U.S. Pat. Nos. 3,589,978 and 4,031,307, and in particular Jaguar C 13 S sold by Meyhall.

4.) Cationic polymers chosen from the group comprising:

a) polymers containing units of the formula: —A—Z—A—Z, in which A denotes a radical containing two amino groups, preferably

and Z denotes the symbol B or B'; B and B', which are identical or different, denote a divalent radical which is a straight-chain or branched-chain alkhylene radical which contains up to 7 consecutive carbon atoms in the main chain, which is unsubstituted or substituted by one or more hydroxyl groups and which can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amine, alkylamine, alkenylamine, benzylamine, amine oxide, quaternary ammonium, amide, imide, alcohol, ester and/or urethane groups; these polymers and the process for their preparation are described in French Patent 2,162,025, the disclosure of which is incorporated by reference.

b) polymers containing units of the formula: —A—Z$_1$—A—Z$_1$—, in which A denotes a radical containing two amino groups, preferably

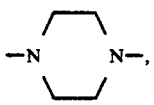

and each Z$_1$ denotes the symbol B$_1$ or B'$_1$ but at least one Z$_1$ denotes the symbol B'$_1$, B$_1$ denotes a divalent radical which is a straight-chain or branched-chain alkylene or hydroxyalkylene radical having up to 7 consecutive carbon atoms in the main chain, and B'$_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more nitrogen atoms, the nitrogen atom being substituted by an alkyl chain which is optionally interrupted by an oxygen atom and which contains one or more hydroxyl groups; these polymers and the process for their preparation are described in French Patent 2,280,361, the disclosure of which is incorporated by reference; and c) the quaternary ammonium salts and the oxidation products of the polymers of the formulae indicated above under a) and b).

5.) Optionally alkylated, crosslinked polyaminopolyamides comprising at least one water-soluble crosslinked polymer obtained by crosslinking a polyamino-polyamide (A) prepared by the polycondensation of an acid compound with a polyamine. The acid compound is chosen from: (i) organic dicarboxylic acids, (ii) aliphatic monocarboxylic and dicarboxylic acids with a double bond, (iii) the esters of the above-mentioned acids, preferably the esters with lower alkanols having from 1 to 6 carbon atoms, and (iv) mixtures of these compounds. The polyamine is chosen from amongst bis-primary, mono-secondary or bis-secondary polyalkylene-polyamines. Up to 40 mol % of this polyamine can be replaced by a bis-primary diamine, preferably ethylenediamine, or by a bis-secondary amine, preferably piperazine, and up to 20 mol % can be replaced by hexamethylenediamine. The crosslinking is carried out by means of a crosslinking agent (B) which is an epihalogenohydrin, diepoxide, dianhydride, unsaturated anhydride or bis-unsaturated derivative. The cross-linking is characterised in that it is carried out by means of 0.025 to 0.35 mol of crosslinking agent per amine group of the polyaminopolyamide (A), generally by means of 0.025 to about 0.2 and in particular by means of 0.025 to about 0.1 mol of crosslinking agent per amine group of the polyaminopolyamide (A). These polymers and their preparation are described in greater detail in French Patent No. 2,252,840, the disclosure of which is incorporated by reference.

These crosslinked polymers are soluble in water to a concentration of 10% without gel formation; the viscosity of a 10% strength solution in water at 25° C. is at least 3 centipoises and usually from 3 to 200 centipoises.

The polyaminopolyamides (A) themselves can also be used according to the invention.

6.) The water-soluble crosslinked polyaminoamides obtained by crosslinking a polyaminopolyamide (A) (described above) by means of a crosslinking agent chosen from:

(I) a compound which is (1) a bis-halogenohydrin, (2) a bis-azetidinium compound, (3) a bishalogenoacyl-diamine and (4) an alkylene dihalide;

(II) the oligomers obtained by reacting a compound (a) which is (1) a bis-halogenohydrin, (2) a bis-azetidinium compound, (3) a bis-halogenoacyl diamine, (4) an alkylene dihalide, (5) an epihalogenohydrin, (6) a diepoxide and (7) a bis-unsaturated derivative, with a compound (b) which is a difunctional compound which is reactive towards the compound (a); and (III) the quaternisation product of a compound (a) or an oligomer (II) and containing one or more tertiary amine groups which can be totally or partially alkylated, with an alkylating agent (c), preferably methyl or ethyl chloride, bromide, iodide, sulphate, mesylate or tosylate, benzyl chloride or bromide, ethylene oxide, propylene oxide or glycidol. The crosslinking is carried out by means of 0.025 to 0.35 mol, in particularly by means of 0.025 to 0.2 mol and more particularly by means of 0.025 to 0.1 mol of crosslinking agent per amine group of the polyaminopolyamide.

These crosslinking agents and these polymers, and also the process for their preparation, are described in French Patent Application No. 2,368,508.

7.) The polyaminoamide derivatives resulting from the condensation of polyalkylenepolyamines with polycarboxylic acids, followed by alkylation by means of difunctional agents. Examples which may be mentioned are adipic acid/dialkylaminohydroxyalkyl-dialkylenetriamine copolymers in which the alkyl radical contains from 1 to 4 carbon atoms and preferably denotes methyl, ethyl or propyl, which are described in French Patent 1,583,363.

Amongst these derivatives, there may be mentioned the adipic acid/dimethylaminohydroxypropyldiethylenetriamine polymers sold under the name Cartaretine F, F$_4$ or F$_8$ by SANDOZ.

8.) The polymers obtained by reacting a polyalkylene-polyamine containing two primary amine groups and at least one secondary amine group with a dicarboxylic acid chosen from diglycolic acid and saturated aliphatic dicarboxylic acids having from 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine group of the polyamide of 0.5:1 to 1.8:1; these polymers are mentioned in U.S. Pat. Nos. 3,227,615 and 2,961,347.

The polymers of this type are especially that sold under the name HERCOSETT 57 by Hercules Incorporated, which has a viscosity at 25° C. of 30 cps in 10% strength aqueous solution, and that sold under the name PD 170 or DELSETTE 101 by Hercules, in the case of the adipic acid/epoxypropyldiethylenetriamine copolymer.

9.) Cyclic polymers having a molecular weight of 20,000 to 3,000,000, such as the homopolymers containing, as the main constituent of the chain, units corresponding to the formula (VII) or (VII'):

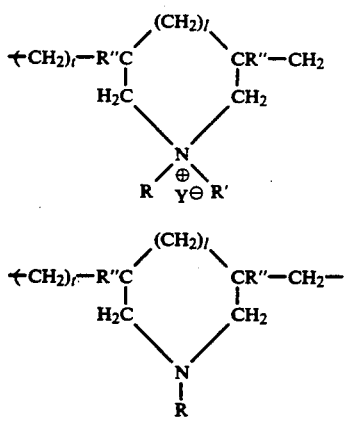

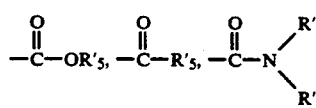

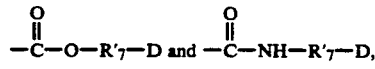

in which l and t are equal to 0 or 1 with the sum l+t=1, R" denotes hydrogen or methyl, R and R' independently of one another denote an alkyl group having from 1 to 22 carbon atoms, a hydroxyalkyl group in which the alkyl group preferably has 1 to 5 carbon atoms, or a lower (generally from 1 to 6, especially 1 to 4, carbon atoms) amidoalkyl group, or R and R' denote, together with the nitrogen atom to which they are attached, a heterocyclic group such as piperidinyl or morpholinyl, and $Y^{\ominus}$ is an anion, such as bromide, chloride, acetate, borate, citrate, tartrate, bisulphate, bisulphite, sulphate or phosphate, and also the copolymers containing units of the formula VII or VII' and units derived from acrylamide or from diacetone-acrylamide.

Amongst the quaternary ammonium polymers of the type defined above, there may be mentioned the dimethyldiallylammonium chloride homopolymer sold under the name MERQUAT 100, which has a molecular weight of less than 100,000, and the dimethyldiallylammonium chloride/acrylamide copolymer having a molecular weight of more than 500,000, which is sold under the name MERQUAT 550 by MERCK.

These polymers are described in French Patent 2,080,759 and its Certificate of Addition No. 2,190,406.

10.) Poly-(quaternary ammonium) compounds containing repeat units of the formula:

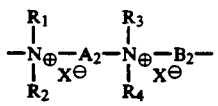

in which $R_1$ and $R_2$, and $R_3$ and $R_4$, which are identical or different, represent aliphatic, alicyclic or arylaliphatic radicals containing at most 20 carbon atoms, or lower hydroxyaliphatic radicals, or alternatively $R_1$ and $R_2$ and/or $R_3$ and $R_4$ form, with the nitrogen atom to which they are attached, a heterocyclic ring optionally containing a second hetero-atom other than nitrogen, or alternatively $R_1$, $R_2$, $R_3$ and $R_4$ represent a group:

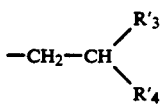

in which $R'_3$ denotes hydrogen or lower alkyl and $R'_4$ denotes one of the following groups: —CN,

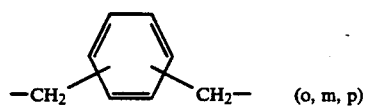

$R'_5$ denoting a lower alkyl group, $R'_6$ denoting hydrogen or a lower alkyl group, $R'_7$ denoting alkylene and D denoting a quaternary ammonium group, $A_2$ and $B_2$ independently represent polymethylene groups containing from 2 to 20 carbon atoms, which can be linear or branched and saturated or unsaturated and which can contain, inserted in the main chain, one or more aromatic rings such as the group:

or one or more groups:

—(CH$_2$)$_n$—Y$_1$—(CH$_2$)$_n$—, $Y_1$ denoting O, S, SO, SO$_2$,

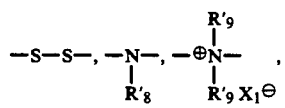

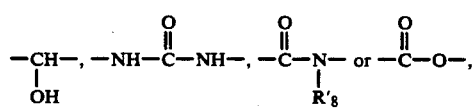

with $X^{\ominus}$ denoting an anion derived from a mineral or organic acid, n being 2 or 3, $R'_8$ denoting hydrogen or a lower alkyl group and $R'_9$ denoting lower alkyl, or alternatively $A_2$, $R_1$ and $R_3$ form a piperazine ring with the two nitrogen atoms to which they are attached; moreover, if $A_2$ denotes a linear or branched, saturated or unsaturated aliphatic or hydroxyl aliphatic radical, $B_2$ can also denote a group:

—(CH$_2$)$_n$—CO—D—OC—(CH$_2$)$_n$— in which D denotes:

a) a glycol radical of the formula —O—Z—O, in which Z denotes a linear or branched hydrocarbon radical or a group corresponding to the formulae:

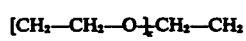

or

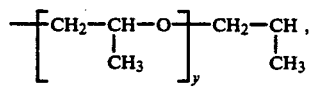

in which x and y denote an integer from 1 to 4, representing a definite and unique degree of polymerisation, or, in a mixture, any number from 1 to 4, representing an average degree of polymerisation;

b) a bis-secondary diamino radical, such as a piperazine derivative of the formula:

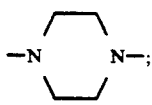

c) a bis-primary diamino radical of the formula:

—NH—Y—NH—, in which Y denotes a linear or branched hydrocarbon radical or the divalent radical

or d) a ureylene group of the formula —NH—CO—NH; and $X^-$ is an anion such as chloride or bromide.

These solvents generally have a molecular weight of 1,000 to 100,000.

Polymers of this type are described, in particular, in French Patents 2,320,330 and 2,270,846, French Applications 2,316,271, 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

11.) Homopolymers or copolymers derived from acrylic or methacrylic acid and containing the unit:

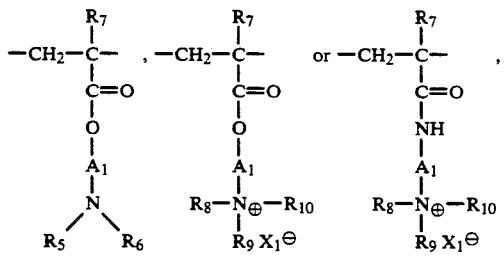

in which $R_7$ is H or $CH_3$, $A_1$ is a linear or branched alkyl group having 1 to 6 carbon atoms or a hydroxyalkyl group having 1 to 4 carbon atoms, $R_8$, $R_9$ and $R_{10}$, which are identical or different, represent an alkyl group having from 1 to 18 carbon atoms or a benzyl group, $R_5$ and $R_6$ represent hydrogen or an alkyl group having from 1 to 6 carbon atoms, and $X_1^{\ominus}$ denotes halogen, such as chlorine or bromine, or methosulphate.

The comonomer or comonomers which can be used include: acrylamide, methacrylamide, diacetone-acrylamide, acrylamide and methacrylamide substituted on the nitrogen by lower alkyl, alkyl esters of acrylic and methacrylic acids, vinylpyrrolidone and vinyl esters.

The following may be mentioned as examples:

the acrylamide/beta-methacryloloxyethyltrimethylammonium methosulphate copolymer sold under the names Reten 205, 210, 220 and 240 by Hercules, the ethyl methacrylate/oleyl methacrylate/beta-methacryloyloxyethyldiethylmethylammonium methosulphate copolymers listed under the name Quaternium 38 in the Cosmetic Ingredient Dictionary, the ethyl methacrylate/abietyl methacrylate/beta-methacryloyloxyethyldiethylmethylammonium methosulphate copolymer misted under the name Quaternium 37 in the Cosmetic Ingredient Dictionary, the beta-methacryloyloxyethyltrimethylammonium bromide polymer listed under the name Quaternium 49 in the Cosmetic Ingredient Dictionary, the beta-methacryloyloxyethyltrimethylammonium methosulphate/beta-methacryloyloxyethylstearyldimethylammonium methosulphate copolymer listed under the name Quaternium 42 in the Cosmetic Ingredient Dictionary, the aminoethylacrylate phosphate/acrylate copolymer sold under the name Catrex by National Starch, which has a viscosity of 700 cps at 25° C. in an 18% strength aqueous solution, and the graft and crosslinked cationic copolymers, having a molecular weight of 10,000 to 1,000,000 and preferably of 15,000 to 500,000, which result from the copolymerisation of:

a) at least one cosmetic monomer,
b) dimethylaminoethyl metharcylate,
c) polyethylene glycol, and
d) a polyunsaturated crosslinking agent, these polymers being described in French Patent 2,189,434.

The crosslinking agent is typically: ethylene glycol dimethacrylate, a diallyl phthalate, divinylbenzene, tetraallyloxyethane or polyallylsucrose having from 2 to 5 allyl groups per mol of sucrose.

The cosmetic monomer can be of a very wide variety of types, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkyl vinyl ether in which the alkyl radical contains from 2 to 18 carbon atoms, an olefin having from 4 to 18 carbon atoms, a vinyl heterocyclic derivative, a dialkyl or N,N-dialkylaminoalkyl maleate in which the alkyl radicals have from 1 to 3 carbon atoms, or the anhydride of an unsaturated acid.

12.) Quaternary polymers of vinylpyrrolidone and vinylimidazole, such as Luviquat FC 905 sold by BASF.

13. ) Cationic silicone polymers, for example those described in European Applications 17,121 and 17,122, U.S. Pat. No. 4,185,087, Japanese Patent Application 80/66506 and Austrian Patent Application 71/01171, the disclosure of which is incorporated by reference, and also those mentioned in the CTFA dictionary under the name AMODIMETHICONE, such as the product marketed as a mixture with other ingredients under the name "Dow Corning 929" cationic emulsion.

14.) Cationic derivatives of starches or of starch ethers, such as those described in French Patent Application 2,434,821, the disclosure of which is incorporated by reference, in particular the polymer sold under the name LAB 358 by ROQUETTE.

Other cationic polymers which can be used include polyalkyleneimines, and in particular polyethyleneimines, polymers containing vinylpyridine units or vinylpyridinium units in the chain, condensates of polyamines and epichlorohydrin, poly-(quaternary ureylene) compounds and chitin derivatives.

The cationic derivatives other than the polymers which can be used in combination with the amphoteric polymers defined above may be quaternary nitrogen derivatives and fatty amines and diamines.

In this respect, there may be mentioned alkyltrimethylammonium chlorides, bromides and p-toluenesulphonates, such as AKYPOQUAT 131 from DSM; dialkyldimethylammonium chlorides and bromides, such as NORAMIUM M2SH and NORAMIUM M2C from PIERREFITTE AUBY; alkylmethyldipolyoxyethyleneammonium chlorides, such as ETHOQUAD C12 from ARMAK; dialkyldipolyoxyethyleneammonium sulphates and alkyltripolyoxyethyleneammonium chlorides or phosphates; polyoxypropylenemethyldiethylammonium chlorides, alkyldimethylhydroxyethylammonium chlorides and alkylpyridinium chlorides; alkylethylmorpholinium ethosulphates; alkylisoquinolinium chlorides and bromides; alkyldimethylbenzylammonium chlorides, bromides and saccharinates; alkylbenzyltrimethylammonium chlorides; alkylbenzyltri-($\beta$-hydroxyethyl)-ammonium chlorides; alkyldimethylalkylbenzylammonium cyclohexylsulphonates; alkylxylyl-bis-(trimethylammonium) chlorides; alkyl-(2-phenoxyethyl)-ammonium bromides; alkylamidropropyldimethylthydroxyethylammonium chlorides; alkylamidopropyldiethylhydroxyethylammonium chlorides; and alkylamidopropyldimethylacetamidoammonium chlorides.

The salts of fatty amines or diamines are chosen, in particular, from amongst alkylamine acetates and hydrochlorides, such as the product sold under the name CATIGENE JR by STEPAN; alkylamidodiethylamines soluble on neutralisation, such as the product sold under the name MIRAMINE ST by MIRANOL or the product sold under the name CHEMICAL BASE 6532 by SANDOZ; fatty diamines, such as the product sold under the name CEMULCAT ODO-ODS by SFOS or the product sold under the name INIPOL 002-SO2 by PIERREFITTE AUBY; fatty diamines giving soluble salts, sold under the name DINORAM C-S-O by PIERREFITTE AUBY; the fatty acid/hydroxyethylethylenediamine condensation products sold, in particular, under the name CERANINE HC 39 B by SANDOZ; alkylamidoethylpolyhydroxyethylammonium hydrochlorides, such as the product called PC 735 and sold by ATLAS; and ethylhydroxymethylalkyloxazolines, such as AKATERGE sold by IMC.

There may also be mentioned quaternary gluconamide halides, such as those described in U.S. Pat. No. 3,766,267, cationic protein hydrolysates, quaternary halides of mink oil amide, such as those described in U.S. Pat. No. 4,012,398, quaternary derivatives of fatty halogenoalkanoates of dialkylaminopropylamide, such as those described in U.S. Pat. No. 4,038,294, and quaternary ammonium derivatives of lanolin fatty acids, such as those described in U.S. Pat. No. 4,069,347.

The cationic derivatives which are more particularly preferred are chosen from amongst the cationic polymers of groups, 1, 2, 9, 10, 12 and 13 and cationic surface-active agents chosen from amongst distearyldimethylammonium chloride, stearyldimethylbenzylammonium chloride or mixtures thereof. The best results are obtained with the preferred amphoteric polymer defined above.

In the preferred embodiment, in addition to the cationic derivative and the amphoteric polymer defined above, the compositions also contain an anionic, non-ionic or amphoteric surface-active agent or a mixture thereof, which are in themselves well known to those skilled in the art and serve, in particular, to solubilise the specified combination.

Amongst the anionic surface-active agents which can be used by themselves or in a mixture, there may be mentioned, in particular, the alkali metal salts, the ammonium salts, the amine salts or the aminoalcohol salts of the following compounds:

alkyl-sulphates, alkyl-ether-sulphates, alkylamidesulphates and alkylamide-ether-sulphates, alkylarylpolyether-sulphates and monoglyceride-sulphates, alkylsulphonates, alkylamidesulphonates, alkylarylsulphonates, $\alpha$-olefinesulphonates and paraffinsulphonates, alkyl-sulphosuccinates-alkyl-ether-sulphosuccinates and alkylamide-sulphosuccinates, alkyl-sulphosuccinamates, alkyl-sulphoacetates and alkyl-polyglycerolcarboxylates, alkyl-phosphates and alkyl-ether-phosphates, and alkylsarcosinates, alkylpolypeptidates, alkylamidopolypeptidates, alkylisethionates and alkyltaurates.

The alkyl radical in all these compounds is generally a linear chain having 12 to 18 carbon atoms.

Other anionic surface-active agents which can be used include fatty acids such as oleic acid, ricinoleic acid, palmitic acid, stearic acid and acids derived from copra oil or from hydrogenated copra oil.

The following may also be mentioned:

acyllactylates in which the alkyl radical contains from 8 to 20 carbon atoms, and carboxylic acids of polyglycol ethers, corresponding to the formula:

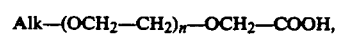

Alk—(OCH$_2$—CH$_2$)$_n$—OCH$_2$—COOH, in the form of bases or salts, in which the substituent Alk corresponds to a linear chain having from 12 to 18 carbon atoms and in which n is an integer from 5 to 15.

Amongst the non-ionic surface-active agents which can be used by themselves or in a mixtures, there may be mentioned, i particular: polyoxyethyleneated, polyoxypropyleneated or polyglycerolated alcohols, alkylphenols and fatty acids with a linear fatty chain containing 8 to 18 carbon atoms and most frequently containing 2 to 30 mols of ethylene oxide. There may also be mentioned copolymers of ethylene oxide and propylene oxide, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters, and fatty acid esters of glucose derivatives.

Other compounds included in this class are: condensation products of a monoalcohol, an $\alpha$-diol, an alkylphenol, an amide or a diglycolamide with glycidol, such as:

R$_4$—CHOH—CH$_2$—O—(CH$_2$—CHOH—CH$_2$—O)$_n$H, in which R$_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p is from 1 to 10, such as the products described in French Patent 2,091,516; compounds corresponding to the formula:

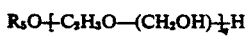

in which $R_5$ denotes an alkyl, alkenyl or alkylaryl radical and q has a statistical value of 1 to 10, such as the compounds described in French Patent 1,477,048; and compounds corresponding to the formula:

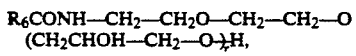

in which $R_6$ denotes a linear or branched, saturated or unsaturated aliphatic radical, or a mixture of such radicals, which can optionally contain one or more hydroxyl groups, which as 8 to 30 carbon atoms and which is of natural or synthetic origin, and r represents an integer or decimal number from 1 to 5 and denotes the average degree of condensation, in a mixture, such as the compounds described in French Patent 2,328,763.

Amongst the amphoteric surface-active agents which can be used, there may be mentioned, more particularly, alkylamino-monopropionates and alkylamino-dipropionates, betaines such as N-alkylbetaines, N-alkylsulphobetaines and N-alkylamidobetaines, cycloimidinium compounds such as alkylimidazolines, and asparagine derivatives.

It is self-evident that the abovementioned surface-active agents can be used not only as solubilising agents but also for taking advantage, either simultaneously with or independently of the abovementioned effect, of their foaming, wetting, detergent, dispersing or emulsifying properties.

The compositions according to the invention can contain cosmetically acceptable solvents such as monoalcohols, polyalcohols, glycol ethers, esters and methylene chloride, which act as solubilisers.

If the composition also contains a solubilising agent, this agent, which can be a single agent of the type mentioned above or a mixture of two or more agents of the type defined above, is suitably present in an amount of 0.1 to 70% and preferably 0.5 to 50% of the total weight of the composition.

The compositions according to the present invention can be used as such for the purpose of treating the hair or skin, or can serve as a "base or carrier" forming part of cosmetic formulations which also contain an effective amount of active product and which are intended for application to the skin or hair in order to protect it against attack from, say, atmospheric agents or actinic rays, and also for promoting the action of any other active product intended for the skin, hair or nails.

The compositions according to the present invention are suitably presented in the form of thickened or non-thickened, aqueous or aqueous-alcoholic solutions, creams, gels, dispersions, emulsions, aerosol foams or sprays; they can also be presented in the form of powders or lyophilisates to be diluted in a suitable carrier at the time of use.

In addition to the amphotetic polymer or polymers and the cationic derivative or derivatives, they can contain adjuvants normally used in cosmetics, such as perfumes, dyestuffs which can serve to colour either the composition itself or the hair, skin or nails, preservatives, sequestering agents, thickeners, emulsifying agents, softeners, electrolytes, non-ionic or anionic polymers and foam stabilisers, depending on the application envisaged.

The compositions can also contain electrolytes such as alkali metal salts and in particular sodium, potassium or lithium salts, these salts preferably being halides, such as the chloride or bromide, sulphates, carbonates or salts of organic acids, such as acetates or lactates, in concentrations not exceeding 10% and preferably 0.5 to 5% by weight.

If the cosmetic compositions as defined above are used for treating the hair, they can be presented, more particularly, in the form of colouring or bleaching products, shampoos, rinsing lotions or creams to be applied before or after shampooing, before or after colouring or bleaching or before or after perming or straightening, setting lotions, blow-drying lotions, restructuring lotions, perming lotions or straightening lotions, and can be dispensed in the form of aerosol foams or sprays.

When the compositions are in the form of shampoos, the concentration of surface-active agent is generally from 3 to 50%, and preferably from 3 to 20%, by weight, and the pH is generally from 3 to 10.

Another embodiment consists of rinsing lotions to be applied mainly before or after shampooing. These lotions are typically aqueous or aqueous-alcoholic solutions, emulsions, thickened lotions or gels.

If the composition are presented in the form of emulsions, they can be non-ionic or anionic. The non-ionic emulsions consist mainly of a mixture of an oil and/or a fatty alcohol with a polyoxyethyleneated alcohol, such as polyoxyethyleneated stearyl or cetyl-stearyl alcohol. Cationic surface-active agents such as those defined above can be added to these compositions.

The anionic emulsions are essentially made up from soaps.

If the compositions are presented in the form of thickened lotions or gels, they contain thickeners, in the presence or absence of solvents. The thickeners which can be used include sodium alginate, gum arabic or cellulose derivatives such as methylcellulose, hydroxymethylcellulose, hydroxyethylcellulose, hydroxypropylcellulose or hydroxylpropylmethylcellulose. The lotions can also be thickened by means of a mixture of a polyethylene glycol and a polyethylene glycol stearate or distearate or by means of a mixture of a phosphoric acid ester and an amide. The concentration of thickener is suitably from 0.5 to 30% by weight and preferably from 0.5 to 15% by weight. The pH of the rinsing lotions is generally from 3 to 9.

If the compositions according to the invention are presented in the form of styling lotions, shaping lotions or so-called setting lotions, they generally comprise, in aqueous alcoholic or aqueous-alcoholic solution, the components of the combination defined above, together, if appropriate, with non-ionic polymers and anti-foam agents.

If the compositions of the present invention are in the form of dyeing compositions for keratin fibres, they contain, in addition to the amphoteric polymer (or polymers) and the cationic derivative (or derivatives), at least one oxidation dyestuff precursor and/or one direct dyestuff and, if appropriate, various adjuvants enabling them to be presented in the form of creams, gels or solutions described above.

They can also contain antioxidants, sequestering agents or any other adjuvant normally used in this type of composition.

The pH of these dyeing compositions is generally from 7 to 11 and it can be adjusted to the desired value by adding an alkalising agent such as ammonia, an alkali metal hydroxide, alkali metal or ammonium carbonate, an alkylamine, alkanolamine or a mixture thereof.

Again, the combination according to the invention can be provided in compositions intended for waving or straightening the hair. This composition contains, in addition to the amphoteric polymer (or polymers) and the cationic derivative (or derivatives), one or more reducing agents, and if appropriate, other adjuvants normally used in this type of composition, and is used in conjunction with a neutralising composition.

The reducing agents which can be used include sulphites, mercaptans and, more particularly, thioglycolates, thiolactates or a mixture thereof.

The neutralising composition contains an oxidising agent which is typically hydrogen peroxide or an alkali metal bromate or perborate.

These compositions can also be packaged as aerosols, in which case they can be applied either in the form of aerosol sprays or in the form of aerosol foams.

If the compositions according to the present invention are dispensed in the form of aerosol foams, the propellant gases used to pressurise the cosmetic formulations are suitably present in an amount not exceeding 25% and preferably 15%, relative to the total weight of the composition. Propellant gases which can be used include carbon dioxide, nitrogen, nitrous oxide, volatile hydrocarbons such as butane, isobutane, propane and mixtures thereof, and non-hydrolysable chlorohydrocarbons and/or fluorohydrocarbons such as those sold under the name FREON by Du Pont de Nemours, in particular the fluorochlorohydrocarbons, such as dichlorodifluoromethane or Freon 12 and dichlorotetrafluoroethane or Freon 114. These propellants can be used by themselves or in combination; the mixture of Freon 114/12 in proportions vary from 40:60 to 80:20 may be mentioned in particular.

The present invention also provides a process for the preparation of a foam which collapses on contact with the hair and which is based on amphoteric polymers defined above and on cationic derivatives, characterised in that this foam is obtained from a composition such as defined above and pressurized in an aerosol device.

The invention also provides the foam thus formed, which is essentially characterised in that it has a density of less than 0.4 and preferably of less than 0.25, and in that it collapses, that is to say that it disappears very rapidly, on contact with the hair after massaging. The disappearance time is less than 1 minute and preferably less than 30 seconds.

The pH of these compositions can be adjusted with an alkalising or acidifying agent normally used in the field of cosmetics. The pH is generally from 3 to 10, depending on the application envisaged. It can be adjusted using alkalising or acidfying agents which are well known in the state of the art.

Another embodiment of the process according to the invention consists in forming the combination of the cationic derivative and the amphoteric polymer on the fibres, and in particular on the hair, by applying, in a first step, a composition, for example in the form of a pre-lotion, containing the cationic polymer, and in a second state, a composition, such as a shampoo or a dye, containing the amphoteric polymer such as defined above.

According to another variant of the invention, a shampoo containing the cationic polymer can be applied in a first step and a composition, such as a lotion, containing the amphoteric polymer can be applied in a second step.

Another possible procedure is to use a perming, straightening, colouring or bleaching composition containing the cationic polymer, and to follow the treatment with this first composition by a treatment with a composition containing the amphoteric polymer, the latter being placed in a composition which can be a shampoo, an oxidising solution or a simple lotion.

Another possible procedure is to use successively a first shampoo containing the cationic derivative and, in a second step, a second shampoo containing the amphoteric polymer, it being possible for the pH of the compositions applied in these two steps to be different and to be adjusted so that, at the time of application of the composition containing the amphoteric polymer, the pH conditions permit a good deposition of the combination according to the invention on the fibres to be treated.

If the compositions are used for application to the skin, they can be presented in the form of after-shave lotions, toilet waters or shaving foams.

The Examples which follow further illustrate the present invention.

EXAMPLE 1

A shampoo having the following composition is prepared:

Non-ionic surface-active agent of the composition: $RCHOH-CH_2O+CH_2-CHOH-CH_2O\frac{1}{n}H$, in which

| | |
|---|---|
| R = $C_9-C_{12}$-alkyl and $\bar{n}$ = 3.5 (statistical value) | 10 g |
| Epichlorohydrin/piperazine polycondensate of molecular weight 1,500 to 2,000 | 1 g |
| Amphoteric polymer sold under the name AMPHOSET by Mitsubishi Petrochemical (a product containing 50% of active ingredient in ethanol) | 0.8 g |
| Water, perfume, preservative, dyestuff q.s. pH adjusted to 7.2 with citric acid. | 100 g |

This shampoo, applied to dirty hair, possesses a good foaming power and provides the dried hair with liveliness, bulk and stiffness on styling.

EXAMPLE 2

A rinse-off after-shampoo having the following composition is prepared:

| | |
|---|---|
| Distearyldimethylammonium chloride | 1 g |
| Cationic silicone polymer sold under the name "DOW CORNING DC 929 cationic emulsion" by Dow Corning (a product containing 35% of active ingredient) | 2.5 g |
| Amphoteric polymer sold under the name AMPHOSET by Mitsubishi Petrochemical (a product containing 50% of active ingredient in ethanol) | 0.6 g |
| Water, perfume, preservative, dyestuff q.s. pH adjusted to 7 with sodium hydroxide. | 100 g |

This composition can be packaged as an aerosol according to the formulation:

| | |
|---|---|
| Composition | 90 g |
| Freon 12/114 propellant | 10 g |

-continued

| | |
|---|---|
| (50/50 by weight) | 100 g |

This after-shampoo, applied to washed and towel-dried hair and rinsed off after a few minutes, makes the wet hair easier to comb out and provides the dried hair with manageability, shine and a hold effect, whilst at the same time preserving a certain suppleness of the hair.

Good comb-out and hold properties are also observed without the hair being rinsed.

EXAMPLE 3

A rinsing lotion having the following composition is prepared:

| | |
|---|---|
| Tetradecyltrimethylammonium bromide | 0.3 g |
| Amphoteric polymer sold under the name AMPHOSET by Mitsubishi Petrochemical (a product containing 50% in ethanol) | 1.6 g |
| Water, perfume, preservative, dyestuff q.s. | 100 g |
| pH adjusted to 7 with hydrochloric acid. | |

This composition, applied to washed and towel-dried hair and rinsed off after a few minutes, provides the dried hair with more volume and hold.

EXAMPLE 4

A rinse-off after-shampoo having the following composition is prepared:

| | |
|---|---|
| Betainised amphoteric polymer sold, as a product containing 50% of active ingredient in ethanol, under the name AMERSETTE by AMERCHOL | 3 g |
| Mixture of cetyl-stearyl alcohol and cetyl-stearyl alcohol oxyethyleneated with 15 mols of ethylene oxide | 3 g |
| Hydroxyethylcellulose sold under the name Cellosize QP 4400H by UNION CARBIDE | 0.6 g |
| Mixture of fatty alcohols and oxyethyleneated products, sold under the name POLAWAX GP 200 by CRIDA | 1.5 g |
| Oleyldimethylbenzylammonium chloride sold under the name AMMONYX KP by FRANCONYX | 0.3 g |
| Vinylpyrrolidone/vinylimidazole copolymer sold, as a product containing 40% of active ingredient, under the name LUVIQUAT FC 904 by B.A.S.F. | 2.2 g |
| Water, perfume, preservative, dyestuff q.s. | 100 g |
| pH = 7.1 with hydrochloric acid. | |

When this product is applied to wet and washed hair, the hair is easy to comb out in the wet state and, after drying, is shiny and easy to comb out and has a good hold.

EXAMPLE 5

A rinsing lotion having the following composition is prepared:

| | |
|---|---|
| Betainised amphoteric polymer sold, as a product containing 50% in ethanol, by AMERCHOL under the name AMERSETTE | 1 g |
| Stearyldimethylbenzylammonium chloride | 0.3 g |
| Water, perfume, dyestuff, preservative q.s. | 100 g |
| pH = 7.7 with sodium hydroxide. | |

Exactly as above, the dried hair, after rinsing with water, is easy to comb out and has a good hold.

Good comb-out and shine properties are also found without the hair being rinsed with water.

EXAMPLE 6

A rinsing lotion having the following composition is prepared:

| | |
|---|---|
| Poly-[N-[3-(dimethylammonio)-propyl]-N'-[3-(ethyleneoxyethylenedimethylammonio)-propyl]-urea dichloride] sold under the name MIRAPOL A15 by MIRANOL | 0.8 g |
| Betainised amphoteric polymer sold, as a product containing 50% of active ingredient in ethanol, by AMERCHOL under the name AMERSETTE | 4 g |
| Water, perfume, preservative, dyestuff q.s. | 100 g |
| pH = 8 with hydrochloric acid. | |

After rinsing, the hair treated with this lotion is easy to comb out, has a good hold and is soft to the touch.

EXAMPLE 7

A shampoo having the following composition is prepared:

Surface-active agent of the formula: RCHOH—CH$_2$O$\{$CH$_2$CHOH—CH$_2$O$\}_{\bar{n}}$H, in which

| | |
|---|---|
| R = C$_9$–C$_{12}$-alkyl and $\bar{n}$ = 3.5 (statistical value) | 10 g |
| Cetylpyridinium chloride | 0.5 g |
| Betainised amphoteric polymer sold, as a product containing 50% of active ingredient in ethanol, by AMERCHOL under the name AMERSETTE | 1.6 g |
| Water, perfume, preservative, dyestuff q.s. | 100 g |
| pH = 7.6, adjusted with sodium hydroxide. | |

It is found that the hair washed with this shampoo has a good hold when dried and is easy to comb out.

EXAMPLE 8

A shampoo having the following composition is prepared:

| | |
|---|---|
| Alkyl(C$_{12}$–C$_{14}$)-dimethylcarboxymethylammonium hydroxide containing 30% of active ingredient, sold under the name DEHYTON AB 30 by HENKEL | 26 g |
| Surface-active agent of the formula: R$\{$OCH$_2$CH$_2\}_{\bar{n}}$OCH$_2$—COOH, R being a mixture of C$_{12}$–C$_{14}$-alkyl radicals and n being equal to 10, a product containing 90% of active ingredient, sold under the name AKYPO RLM 100 by CHEMY | 7 g |
| Dimethyldiallylammonium chloride/acrylamide copolymer having a molecular weight of more than 500,000, sold under the name MERQUAT 550 by MERCK | 0.25 |
| Betainised amphoteric polymer sold, as a product containing 50% of active ingredient in ethanol, under the name AMERSETTE by AMERCHOL | 2.6 g |
| Water, perfume, preservative q.s. | 100 g |
| pH = 8 with sodium hydroxide. | |

The results found are similar to those observed for the preceding examples.

EXAMPLE 9

A shampoo having the following composition is prepared:

| | |
|---|---|
| Trideceth-7 carboxylic acid of the formula: CH$_3$$\{$CH$_2\}_{11}$—CH$_2$$\{$OCH$_2$CH$_2\}_{\bar{6}}$OCH$_2$COOH, containing 90% of active ingredient, sold | 7 g |

-continued

| | |
|---|---|
| under the name SANDOPAN DTC acid by SANDOZ | |
| Triethanolamine salt of the condensation product of copra acid and animal protein hydrolysate, containing 40% of active ingredient, sold under the name MAYPON 4CT by STEPAN | 15 g |
| Adipic acid/[dimethylaminohydroxypropyl]-diethylenetriamine copolymer sold under the name CARTARETINE F4 by SANDOZ | 0.4 g |
| Betainised amphoteric polymer sold, as a product containing 50% of active ingredient in ethanol, under the name AMERSETTE by AMERCHOL | 1.6 g |
| Water, dyestuff, preservative, perfume q.s. pH = 7 with sodium hydroxide. | 100 g |

Exactly as for the preceding examples, the washed hair is easy to comb out.

EXAMPLE 10

A shampoo having the following composition is prepared:

| | |
|---|---|
| Sodium salt of sulphated alkanol($C_{12}$-$C_{14}$) oxyethyleneated with 2.2 mols of ethylene oxide, containing 25% of active ingredient | 48 g |
| Quaternary polyvinylpyrrolidone copolymer having a molecular weight of 1,000,000 marketed under the name GAFQUAT 755 by GENERAL ANILINE | 0.5 g |
| Betainised amphoteric polymer sold, as a product containing 50% of active ingredient in ethanol, by AMERCHOL under the name AMERSETTE | 1.8 g |
| Water, perfume, preservative, dyestuff q.s. pH = 8 with hydrochloric acid. | 100 g |

The hair washed with this shampoo and rinsed with water is soft to the touch, easy to comb out and shiny.

We claim:

1. A composition for conditioning the hair which comprises, in a solvent medium, at least one cationic polymer selected from the group consisting of:
   1) a quaternised or unquaternised vinylpyrrolidone/dialkylaminoalkyl acrylate or methacrylate copolymer;
   2) a cationic polysaccharide;
   3) a cationic polymer containing units of the formula —A—Z—A—Z— (I), in which A denotes a radical containing two amino groups, and Z denotes the symbol B or B'; B and B', which are identical or different, denote a linear or branched aliphatic radical which is unsubstituted or substituted by one or more hydroxyl groups or contains oxygen, nitrogen or sulphur atoms or 1 to 3 aromatic or heterocyclic rings; or of the formula: —A—Z$_1$—A—Z$_1$— (II), in which A is as defined above and each $Z_1$ independently denotes the symbol $B_1$ or $B'_1$ but denotes $B'_1$ at least once; $B_1$ is a linear or branched alkylene or hydroxyalkylene radical and $B'_1$ is a linear or branched alkylene radical which is unsubstituted or substituted by one or more hydroxyl radicals or which is interrupted by one or more nitrogen atoms, the nitrogen atom being substituted by an alkyl chain or an alkyl chain interrupted by an oxygen atom or an alkyl chain containing one or more hydroxyl groups; or an alkylation product of a polymer of formula (I) or (II) with an alkyl or benzyl halide or a lower alkyl tosylate or mesylate, or an oxidation product of a polymer of formula (I) or (II);
   4) a polyaminopolyamide;
   5) a crosslinked polyaminopolyamide which is:
      a) a crosslinked polyaminopolyamide obtained by crosslinking a polyaminopoloyamide, prepared by the polycondensation of an acid compound with a polyamine, with a crosslinking agent which is an epihalogenohydrin, diepoxide, dianhydride, unsaturated anhydride or bis-unsaturated derivative, the crosslinking agent being used in an amount of 0.025 to 0.35 mole per amine group of the polyaminoamide or an alkylated said crosslinked polyaminopolyamide;
      b) a water-soluble crosslinked polyaminopolyamide obtained by crosslinking a polyaminopolyamide defined above with a crosslinking agent which is:
         I—a bis-halogenohydrin, bis-azetidinium compound, bis-halogenoacyl-diamine or alkylene di-halide,
         II—an oligomer obtained by reacting a compound from group I, or an epihalogenohydrin, diepoxide of bis-unsaturated derivative, with a difunctional compound which is reactive towards these compounds, or
         III—a quaternisation product of a compound from group I or an oligomer from group II, containing tertiary amine groups which can be totally or partially alkylated, with an alkylating agent, the crosslinking being carried out with 0.025 to 0.35 mol of crosslinking agent per amine group of the polyaminopolyamide; or
      c) a polyaminopolyamide derivative resulting from the condensation of a polyalkylene-polyamine with a polycarboxylic acid, followed by alkylation with a difunctional agent;
   6) a polymer obtained by reacting a polyalkylene-polyamine containing two primary amine groups and at least one secondary amine group with a dicarboxylic acid which is diglycolic acid or a saturated aliphatic dicarboxylic acid having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine group of the polyamide of 0.5:1 to 1.8:1;
   7) a cyclic polymer containing chain units corresponding to the formula:

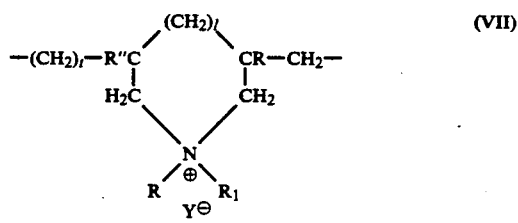
(VII)

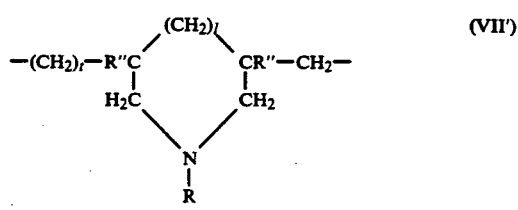
(VII')

in which l and t are equal to 0 or 1 such that l+t=1, R" denotes hydrogen or methyl, R and R' independently of one another denote an alkyl group having 1 to 22 carbon atom, a hydroxyalkyl group, or a lower amidoalkyl group, or R and R' denote, together with the nitrogen atom to which they are attached, a heterocyclic group, and $Y^\ominus$ is an anion, or a copolymer containing units of the formula (VII) or (VII') and units derived from acrylamide or from diacetone-acrylamide;

8) a poly-(quaternary ammonium) compound of the formula:

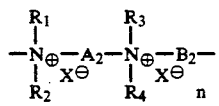
(VIII)

in which $R_1$ and $R_2$, and $R_3$ and $R_4$, which are identical or different, represent an aliphatic, alicyclic or arylaliphatic radical containing at most 20 carbon atoms, or a lower hydroxyaliphatic radical, or $R_1$ and $R_2$ or $R_3$ and $R_4$ together form, with the nitrogen atoms to which they are attached, a heterocyclic ring or a heterocyclic ring containing a second hetero-atom other than nitrogen, or alternatively, $R_1$, $R_2$, $R_3$ and $R_4$ represent the group:

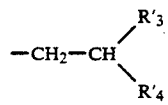

$R'_3$ denoting hydrogen or lower alkyl and $R'_4$ denoting:

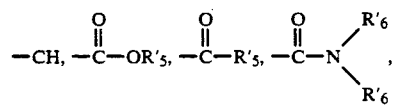

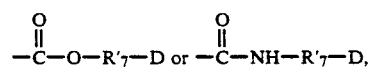

$R'_5$ denoting lower alkyl, $R'_6$ denoting hydrogen or lower alkyl, $R'_7$ denoting alkylene and D denoting a quaternary ammonium group, $A_2$ and $B_2$ independently represent a polyaliphatic group containing from 2 to 20 carbon atoms, which can be linear and saturated or unsaturated or which can contain, inserted in the main chain, one or more aromatic rings or one or more groups $-(CH_2)_n-Y_1-(CH_2)_n-$, with $Y_1$ denoting O, S, SO, $SO_2$, $-S-S-$,

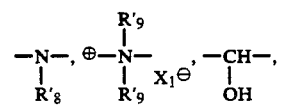

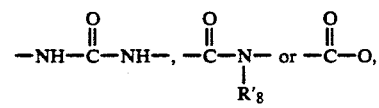

with $X^\ominus_1$ denoting an anion derived from a mineral or organic acid, n being 2 or 3, $R'_8$ denoting hydrogen or lower alkyl and $R'_9$ denoting lower alkyl, or alternatively $A_2$ and $R_1$ and $R_3$ together form a piperazine ring with the two nitrogen atoms to which they are attached; further, if $A_2$ denotes a linear or branched, saturated or unsaturated alkylene or hydroxyalkylene radical, $B_2$ can also denote a group: 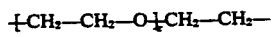, in which D denotes:

a) a glycol radical of the formula $-O-Z-O-$ in which z denotes a linear or branched hydrocarbon radical or a group corresponding to the formula:

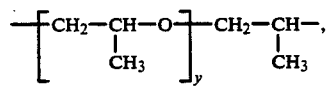

or

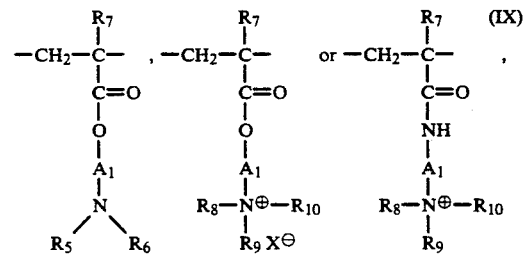

in which x and y denotes an integer from 1 to 4;
b) a bis-secondary diamino radical;
c) a bis-primary diamino radical of the formula: $-NH-Y-NH-$, in which Y denotes a linear or branched hydrocarbon radical or the divalent radical $-CH_2CH_2-S-S-CH_2-CH_2$; or
d) a ureylene group of the formula $-NH-CO-NH-$; n is such that the molecular weight is from 1,000 to 100,000, and $X^\ominus$ denotes an anion;

9) a homopolymer or copolymer derived from acrylic or methacrylic acid and containing at least one unit:

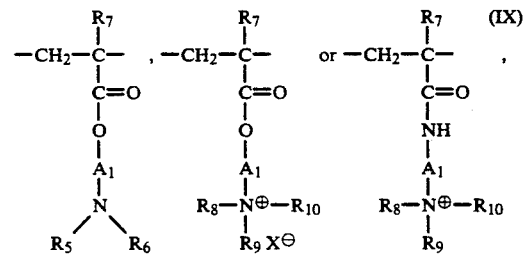
(IX)

in which $R_7$ is H or $CH_3$, $A_1$ is a linear or branched alkyl group having 1 to 6 carbon atoms or a hydroxyalkyl group having 1 to 4 carbon atoms, $R_8$, $R_9$ and $R_{10}$, which are identical or different, denote an alkyl group having 1 to 18 carbon atoms or a benzyl group, $R_5$ and $R_6$ represent H or alkyl having 1 to 6 carbon atoms, and $X_1^\ominus$ denotes a methosulphate or halide anion;

10) a quaternary vinylpyrrolidone/vinylimidazole copolymer;
11) a polyalkyleneimine;
12) a polymer containing vinylpyridine units or vinylpyridinium units in the chain;
13) a condensate of a polyamine and epichlorohydrin;
14) a poly-(quaternary ureylene) compound;
15) a chitin derivative; and
16) a cationic silicone polymer; and at least one amphoteric polymer of betainised dialkylaminoalkyl (meth)acrylate or dialkylaminoalkyl (meth)acrylamide containing units of the formula:

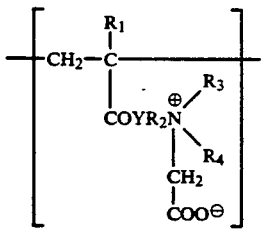

in which $R_1$ denotes a hydrogen atom or a methyl group, $R_2$ denotes an alkylene group having 1 to 4 carbon atoms, Y denotes O or NH and $R_3$ and $R_4$ independently denote a hydrogen atom or an alkyl radical having 1 to 4 carbon atoms.

2. A composition for the treatment of hair to improve the liveliness, shine, body, stiffness, and comb-out properties of the hair and to impart softness to the hair, said composition comprising, in solvent medium, at least one amphoteric polymer of betainised dialkylaminoalkyl (meth)acrylate or dialkylaminoalkyl (meth)acrylamide containing units of the formula:

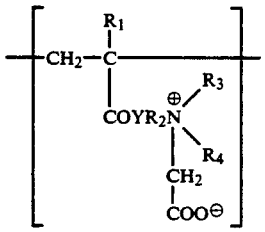

in which $R_1$ denotes a hydrogen atom or a methyl group, $R_2$ denotes an alkylene group having 1 to 4 carbon atoms, Y denotes O or NY and $R_3$ and $R_4$ independently denote a hydrogen atom or an alkyl radical having 1 to 4 carbon atoms; and at least one cationic polymer which is selected from the group consisting of cationic polyamine, polyaminopolyamide and poly(quaternary ammonium) polymer, the amine or quaternary ammonium groups forming part of the polymer chain or being joined thereto, said cationic polymer being other than a quaternary cellulose ether, the amphoteric polymer being present in an amount from 0.01 to 10% by weight, relative to the total weight of the composition, and the cationic polymer being present in an amount from 0.01 to 10% by weight, the polymers having a molecular weight of 500 to 2,000,000.

3. A composition according to claim 2 in which the amphoteric polymer also contains units corresponding to the formula:

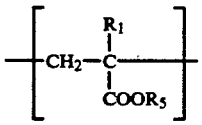

in which $R_1$ is as defined in claim 2 and $R_5$ represents an alkyl or alkenyl radical having from 4 to 24 carbon atoms or a cycloalkyl radical having 4 to 24 carbon atoms.

4. A composition according to claim 3, in which the amphoteric polymer is a terpolymer which contains, in addition to the units of the formula (I) and (II), units of the formula

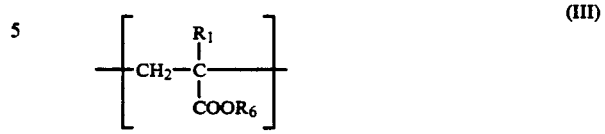

in which $R_6$ denotes an alkyl or alkenyl group having 1 to 3 carbon atoms and $R_1$ is as defined in claim 14.

5. A composition according to claim 3 in which the amphoteric polymer is a copolymer which contains, in addition to the units of the formula (I) and (II), at least one member selected from the group consisting of units derived from a hydrophilic ethylenic monomer (V), and mixture of units derived from a hydrophilic ethylenic monomer (IV) and units of a second, different, ethylenic monomer (V).

6. A composition according to claim 3, in which the amphoteric polymer is a terpolymer, tetrapolymer or pentapolymer which contains, in addition to the units of the formulae (I) and (II), at least one member selected from the group consisting of:

(i) units of the formula

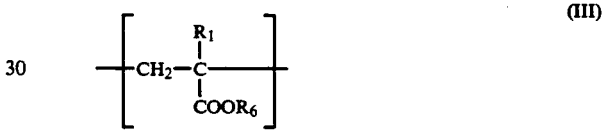

(ii) units derived from a hydrophilic ethylene monomer (IV), (iii) units of a second, different, ethylenic monomer (V), (iv) a mixture of units (ii) and (iii).

7. A composition according to claim 6 wherein the amphoteric polymer is a copolymer containing units of the formulae (I), (II) and (III) in which Y denotes an oxygen atom, $R_2$ denotes the group $-C_2H_4-$, $R_1$, $R_3$ and $R_4$ denote methyl, $R_5$ denotes an alkyl group having 4 to 18 carbon atoms, and $R_6$ denotes an alkyl group having 1 to 3 carbon atoms; and wherein the cationic polymer is poly-[N-[3-(dimethylammonio)-propyl]-N'-[3-(ethyleneoxyethylenedimethylammonio)-propyl]-urea dichloride].

8. A composition according to claim 6 in which the amphoteric polymer is a copolymer containing from 25 to 45% of units of formula (I), from 5 to 65% by weight of units of formula (II), from 0 to 50% by weight of units of formula (III), from 0 to 20% by weight of units of formula (IV) and from 0 to 20% by weight of units of formula (V).

9. A composition according to claim 6 in which the amphoteric polymer is a copolymer which contains at least units of formula (I), (II) and (III), in which Y denotes an oxygen atom, $R_2$ denotes the group $C_2H_4$, $R_1$, $R_3$ and $R_4$ denote methyl, $R_5$ denotes an alkyl group having from 4 to 18 carbon atoms and $R_6$ denotes an alkyl group having 1 to 3 carbon atoms.

10. A composition according to claim 2 which also contains one of more anionic, non-ionic or amphoteric surface-active agents.

11. A composition according to claim 2 which contains one or more of a monoalcohol, polyalcohol, glycol ether, ester or methylene chloride, as solvent.

12. A composition according to claim 2 which also contains a perfume, dyestuff which serves to colour either the composition itself or the hair or skin, preservative, sequestering agent, thickener, emulsifying agent, softener, non-ionic or anionic polymer or foam stabiliser.

13. A composition according to claim 2 which is in the form of a thickened or non-thickened, aqueous, alcoholic or aqueous-alcoholic solution, a cream, a gel or an emulsion, or an aerosol foam or an aerosol spray.

14. A composition according to claim 2 which contains an alkali metal salt in an amount up to 10% by weight.

15. A composition according to claim 2 which is dispensed in the form of an aerosol foam and contains a propellant gas which is cosmetically compatible with the amphoteric polymer and the cationic polymer.

16. A composition according to claim 2 which is in a form selected from the group consisting of a hair conditioner, a colouring product, a bleaching product, a shampoo, a setting lotion, a blow-drying lotion, a restructuring lotion, a perming lotion, a straightening lotion or a rinsing lotion to be applied before or after shampooing, before or after colouring or bleaching or before or after perming or straightening.

17. Process for treating keratin fibers, which comprises applying thereto at least one composition as defined in claim 2.

18. A composition according to claim 9 wherein the amphoteric polymer is a copolymer containing units of the formulae (I), (II) and (III) in which Y denotes an oxygen atom, $R_2$ denotes the group $-C_2H_4-$, $R_1$, $R_3$ and $R_4$ denote methyl, $R_5$ denotes an alkyl group having 4 to 18 carbon atoms, and $R_6$ denotes an alkyl group having 1 to 3 carbon atoms; and wherein the cationic polymer is a quaternary vinylpyrrolidone/vinylimidazole copolymer.

19. A composition according to claim 18 which also contains one or more anionic, non-ionic or amphoteric surface-active agents.

20. A shampoo composition for the hair which comprises, in a solvent medium, an amount of about 3 to 50% of a surface-active agent; at least one amphoteric polymer of betainised dialkylaminoalkyl (meth)acrylate or dialkylaminoalkyl (meth)acrylamide containing units of the formula:

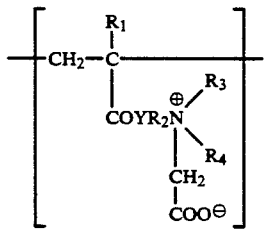

(I)

in which $R_1$ denotes a hydrogen atom or a methyl group, $R_2$ denotes an alkylene group having 1 to 4 carbon atoms; Y denotes O or NH and $R_3$ and $R_4$ independently denote a hydrogen atom or an alkyl radical having 1 to 4 carbon atoms and at least one non-cellulosic ether type cationic polymer which is selected from the group consisting of cationic polyamine, polyaminopolyamide and poly-(quaternary ammonium) polymer, the amine or quaternary ammonium groups forming part of the polymer chain or being joined thereto.

21. A styling, shaping or setting lotion which comprises, in an aqueous, alcoholic or aqueous-alcoholic solution, at least one amphoteric polymer or betainised dialkylaminoalkyl (meth)acrylate or dialkylaminoalkyl (meth)acrylamide containing units of the formula:

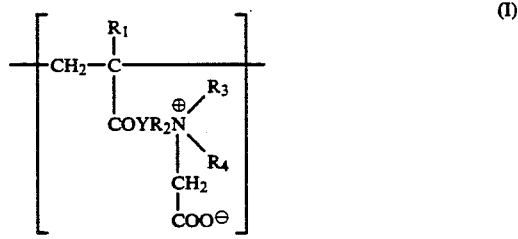

(I)

in which $R_1$ denotes a hydrogen atom or a methyl group, $R_2$ denotes an alkylene group having 1 to 4 carbon atoms; Y denotes O or NH and $R_3$ and $R_4$ independently denote a hydrogen atom or an alkyl radical having 1 to 4 carbon atoms and at least one cationic derivative which is selected from the group consisting of cationic polyamine, polyaminopolyamide and poly-(quaternary ammonium) polymer, the amine or quaternary ammonium groups forming part of the polymer chain or being joined thereto, said cationic derivative being other than a quaternary cellulose ether.

22. A composition for treating the hair which comprises, in a solvent medium, at least one amphoteric polymer of betainised dialkylaminoalkyl (meth)acrylate or dialkylaminoalkyl (meth)acrylamide containing units of the formula:

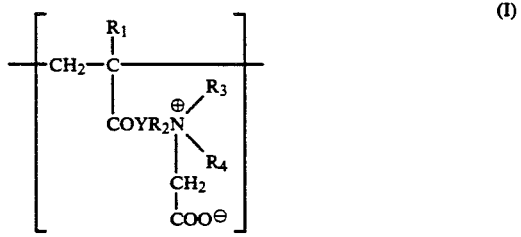

(I)

in which $R_1$ denotes a hydrogen atom or a methyl group, $R_2$ denotes an alkylene group having 1 to 4 carbon atoms, Y denotes O or NH and $R_3$ and $R_4$ independently denote a hydrogen atom or an alkyl radical having 1 to 4 carbon atoms; and a quaternary cellulose derivative, said cellulose derivative being other than a quaternary cellulose ether.

23. A process for treating the hair to impart liveliness, shine, body and comb out properties thereto, which comprises applying to the hair, in a first step, an effective amount of at least one cationic polymer which is selected from the group consisting of cationic polyamines, polyaminopolyamide and poly(quaternary ammonium) polymers, the amine or quaternary ammonium groups of which form part of the polymer chain or are joined thereto, wherein said cationic polymer is other than a quaternary cellulose ether, and, in a second step, applying an effective amount of an amphoteric polymer of betainised dialkylaminoalkyl (meth)acrylate or dialkylaminoalkyl (meth acrylamide which amphoteric polymer contains units of the formula:

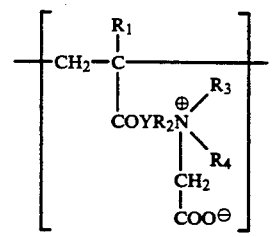

in which $R_1$ denotes a hydrogen atom or a methyl group, $R_2$ denotes an alkylene group having from 1 to 4 carbon atoms, Y denotes O or NH, and $R_3$ and $R_4$ independently denote a hydrogen atom or an alkyl radical having from 1 to 4 carbon atoms, wherein said effective amounts are effective, when applied in successive steps, to impart said liveliness, shine, body and comb out properties to the hair.

* * * * *